(12) United States Patent
Machovic Basic et al.

(10) Patent No.: US 9,027,710 B2
(45) Date of Patent: May 12, 2015

(54) SURGEON LIFT SYSTEM

(75) Inventors: Miriam Machovic Basic, Rancho Palos Verdes, CA (US); Howard S Mellin, Lawndale, CA (US); Faranak Sarbaz, Rancho Palos Verdes, CA (US)

(73) Assignee: Abacus Innovations, Inc, Long Beach, CA (US)

( * ) Notice: Subject to any disclaimer, the term of this patent is extended or adjusted under 35 U.S.C. 154(b) by 1115 days.

(21) Appl. No.: 12/583,982

(22) Filed: Aug. 29, 2009

(65) Prior Publication Data

US 2010/0051386 A1 Mar. 4, 2010

Related U.S. Application Data

(60) Provisional application No. 61/093,224, filed on Aug. 29, 2008.

(51) Int. Cl.
*E04G 1/22* (2006.01)
*A61B 19/00* (2006.01)

(52) U.S. Cl.
CPC .. *A61B 19/28* (2013.01); *E04G 1/22* (2013.01)

(58) Field of Classification Search
CPC ........................................... E04G 1/22
USPC .................. 182/148, 68.4; 5/507.1
See application file for complete search history.

(56) References Cited

U.S. PATENT DOCUMENTS

| | | | |
|---|---|---|---|
| 1,442,664 A * | 1/1923 | Hansen .............................. | 108/5 |
| 3,029,106 A | 4/1962 | McGuire | |
| 3,754,787 A * | 8/1973 | Garber ...................... | 297/195.11 |
| 4,373,761 A * | 2/1983 | Hansberry, Jr. .......... | 312/249.12 |
| 5,029,941 A | 7/1991 | Twisselmann | |
| 5,285,992 A | 2/1994 | Brown | |
| 5,490,716 A * | 2/1996 | Naughton ................ | 297/423.12 |
| 5,540,160 A * | 7/1996 | Rea ............................ | 112/217.2 |
| 5,620,230 A | 4/1997 | Wu | |
| 5,765,910 A * | 6/1998 | Larkin et al. .................. | 297/172 |
| 6,227,614 B1 * | 5/2001 | Rubin ........................... | 297/172 |
| 6,912,749 B2 | 7/2005 | Thomas et al. | |
| 6,928,676 B1 | 8/2005 | Schwaegerle | |
| 7,168,549 B1 * | 1/2007 | Harrison et al. ........... | 198/346.3 |
| 7,234,180 B2 | 6/2007 | Horton et al. | |
| 7,386,899 B2 * | 6/2008 | Smith ............................ | 5/507.1 |
| 2006/0207021 A1 * | 9/2006 | Brunson et al. ............. | 5/81.1 R |
| 2006/0284123 A1 * | 12/2006 | Goldstein .................. | 250/515.1 |
| 2007/0252095 A1 * | 11/2007 | Magram ..................... | 250/515.1 |
| 2010/0219668 A1 * | 9/2010 | Nelson et al. ................. | 297/330 |

FOREIGN PATENT DOCUMENTS

JP 05330797 A * 12/1993

* cited by examiner

*Primary Examiner* — Alvin Chin-Shue
(74) *Attorney, Agent, or Firm* — Vesna Rafaty IP Law PLLC; Vesna Rafaty

(57) ABSTRACT

A surgeon lift comprising a base, wheels attached to the base, each wheel comprising a locking mechanism, a cylinder supported on the base, a platform operatively connected to the cylinder, a lifting mechanism for adjusting the height of the platform relative to a horizontal surface, a connector for operative attachment of the surgeon lift to a surgical table, the surgical table comprising an assembly comprising a power source for receiving the connector, and one or more controllers for automatically controlling the position of the lift relative to the surgical table in the x, y, and z dimensions.

7 Claims, 6 Drawing Sheets

SURGEON LIFT SYSTEM

CLAIM OF PRIORITY

This non-provisional patent application claims priority to Provisional Patent Application No. 61/093,224 entitled "Surgical Lift" which was filed on Aug. 29, 2008 and which is hereby incorporated by reference in its entirely.

FIELD OF THE INVENTION

The present invention relates generally to devices and systems, including improved surgeon lift, surgeon chair, and surgical table for enabling optimal positioning of a surgeon relative to a patient on a surgical table.

BACKGROUND OF THE INVENTION

Surgical procedures are increasingly more complex and often require the surgeon to maintain over a relatively long period of time a fixed bodily posture relative the operative field thereby contributing to surgeon fatigue. This is further exacerbated when the surgeon performs a laparoscopic procedure which requires handling of instrumentation with both hands while maintaining visual control of a video display. Multiple published studies have shown that a surgeon's muscle fatigue increases during the performance of surgical operations. There are numerous published studies showing that ergonomic requirements of a surgeon are not met during the surgery by prior art systems. Notably, the height of the operating table relative to the surgeon may be too high or too low and may thus require the surgeon to assume a less than comfortable position throughout the procedure. While prior art surgical tables are equipped with controls for adjusting the height of the surgical table relative to the floor, the controls have a limited range and importantly are not designed for optimizing the position of the surgical table bed relative to the surgeon. In some situations, the limitations of the height of the operating table can cause the surgeon to operate from a less than optimal angle. Moreover, the position of the patient may make access to the operative field more difficult, and decrease operative field exposure, prolong the surgery time and may increase the chance of an operative complication.

Furthermore, prior art systems do not address the situation when two or more surgeons are required to perform a surgical operation, each needing the ability to independently optimize his/her position relative to the operative field. For example, the surgical table height may be proper for one surgeon but not for another.

Currently, operating rooms are typically supplied with simple surgical stands. A surgical stand is an iron stand of a fixed height for supporting a surgeon in a standing posture. The prior art surgical stand is not adjustable to accommodate the positioning needs of the surgeon or surgical team performing the surgery.

Surgeon chairs are known. See for example U.S. Pat. No. 5,490,716 to Naughton and U.S. Pat. No. 5,029,941 to Twisselmann. Additionally systems of body supports for a surgeon performing a surgical procedure are known. See for example U.S. Pat. No. 3,754,787 to Garber. See also U.S. Patent Application 2006/0207021 to Brunson et al. entitled "Multi-directional personnel lift." However, the applicants are not aware of prior art systems directed at optimizing the ability of a surgical team to readily, precisely, and efficiently control the position of a surgeon(s) relative to a surgical table bed while affording the surgeon and surgical team a requisite freedom of movement that contributes to surgeon comfort.

SUMMARY OF THE INVENTION

The applicant has invented a surgeon lift system that is multipurpose and versatile and specially designed to be responsive to the needs of a surgeon or surgical team to adjust, control, and efficiently maintain a most optimal position of the surgeon relative to the surgical table throughout the duration of a surgical operation, and whether the surgeon sits or stands or takes several steps ('walks') while performing the operation at the surgical table. The disclosed apparatus and system will help a surgeon to quickly and easily and precisely adjust (and maintain as needed) his/her position relative to the operative field while promoting the surgeon's ergonomic comfort.

Three embodiments of the surgeon lift system are disclosed: (1) standalone surgeon lift (suitable for use by one surgeon), (2) standalone surgeon lift comprising a so-called 'walking platform' (suitable for use by one or more surgeons and suitable for taking several steps), (3) surgeon lift with chair combination. The disclosed embodiments comprise a means for operative attachment of the surgeon lift to a surgical table for enabling precise control of the position of the surgeon lift in several dimensions relative to the surgical table. The disclosed invention is also directed to an improved surgical table designed to operatively receive a surgeon lift as described.

Per a preferred embodiment of a stand alone surgeon lift, the surgeon lift comprises a base 14 comprising wheels 28 with wheel breaks or stops (preferably foot-actuated), a platform 12 supported above the base 14, and a platform lifting mechanism for adjustment of the height of the platform relative to a horizontal surface reference point such as the surgical table bed 38 or the floor. The lifting mechanism may comprise a hydraulic lift cylinder 24 and hydraulic pump 26 as shown or the lifting mechanism may be powered using an electric motor or other power mechanism (pneumatic power). The surgeon stands on the platform during a surgery and the platform may be sized to accommodate more than one surgeon. The platform can have any desired shape and configuration. Per the preferred embodiment, the platform is substantially rectangular in shape. Per an alternative first embodiment (not shown), a threading mechanism (in place of the hydraulic cylinder, for example) may be used for adjustment of the height of the platform. The preferred embodiment of the surgeon lift system is a readily movable stand alone surgeon lift that is properly substantially draped with surgical covers and rolled into the surgical suite as/when needed.

The disclosed surgeon lift is also preferably adapted for manual, removable attachment to an improved surgical table as desired for more efficient control of the position of the surgeon lift in the x and z dimensions relative to the surgical table.

The surgeon lift embodiment with so-called walking platform has a platform that is sized to allow one or more surgeons to walk on the platform as needed thereby giving the surgeon(s) access to substantially the entire width of the surgical table without the need to reposition the surgeon lift during the surgical operation. This is a time-saving feature.

Per an optional feature, the angle of the platform may optionally be adjustable if desired for promoting optimal access to the patient in the surgical field. Per such optional feature, a dedicated platform angle controller may be provided.

For purposes of this disclosure, the term 'x dimension' shall generally refer to the separation distance between the leading edge of the surgeon lift and the front of the surgical table, where front refers to the edge of the surgical table that is closest to the surgeon during a surgical operation and where leading edge refers to the side of the platform that faces the surgical table. The term 'y dimension' shall refer to the vertical distance (height) of the platform of the surgeon lift relative to a horizontal reference point, such as the surgical table bed or the floor. The term 'z dimension' shall refer to the axis that captures the separation distance between a side of the platform of the surgeon lift and a side of the surgical table, where a side of the surgical table is perpendicular to the front of the surgical table per above and where a side of the platform is perpendicular to the leading edge of the platform per above.

Per a third embodiment, the disclosed surgeon lift system incorporates a surgeon seat (and preferably an adjustable back support, and optionally, adjustable arm rests, and foot rests) for allowing the surgeon to perform a procedure while seated and while having the benefit of all of the disclosed control features of the disclosed surgeon lift. The surgeon seat may be mounted in any suitable location on the platform. The surgeon seat may be fixedly attached to the platform or preferably, the surgeon seat is securely attached to the platform while allowing for its controlled movement relative to the platform via a wheel rail guide system as shown. Per an optional feature, the surgeon seat may be manually and readily attached to the platform as needed thereby converting the surgeon lift from a standing platform to a platform with a surgeon seat. Alternatively, the surgeon lift with chair combination may be made available with the chair pre-installed on the platform. The platform of the surgeon lift may be designed to accommodate more than one surgeon seat as desired.

Per the preferred embodiment of the disclosed surgeon lift, one or more independent controllers are provided for precise control of the position of the surgeon lift in the x, y, and z dimensions as desired. The control may be pneumatic type or electronic type. Per a preferred embodiment, the surgical lift comprises one controller for automatically controlling the height of the platform relative to the surgical table, and a second controller for automatically controlling the height of the seat portion of the surgeon chair (if used) relative to the surgical table. The surgeon interfaces with the controllers via a control pad that is fixedly mounted on the platform. The controllers are preferably programmable controllers which capture the x, y, and z positional data for a particular position of the surgeon lift thereby saving set-up time in the surgical suite. Thus, the programmable controllers might capture a given surgeon's most preferred (default, or initial) position for the surgeon lift. Remote control of the disclosed surgeon lift by a nurse or surgical assistant is possible. Programmable controllers may be voice activated to enable the surgeon to have both hands free for handling surgical instrumentation and for other surgical tasks. Preferably, the controls are attached to the sterile drapes which cover the patient.

Per a preferred embodiment of the disclosed surgeon lift system, there is provided a surgeon lift 10 comprising a lower platform 14 comprising attached wheels 28, an upper platform 12, a surgeon lift system controller 16, and controller support 18.

Since the disclosed surgeon lift system will be utilized in a surgical suite environment, it will need to be draped with surgical drapes. Proper draping may include placing separate (disposable) surgical drapes on the platform (and the connector platform when used), the control pad, surgeon seat, back rest, foot rest, arm rest.

DETAILED DESCRIPTION OF THE DRAWINGS

Figure 1:
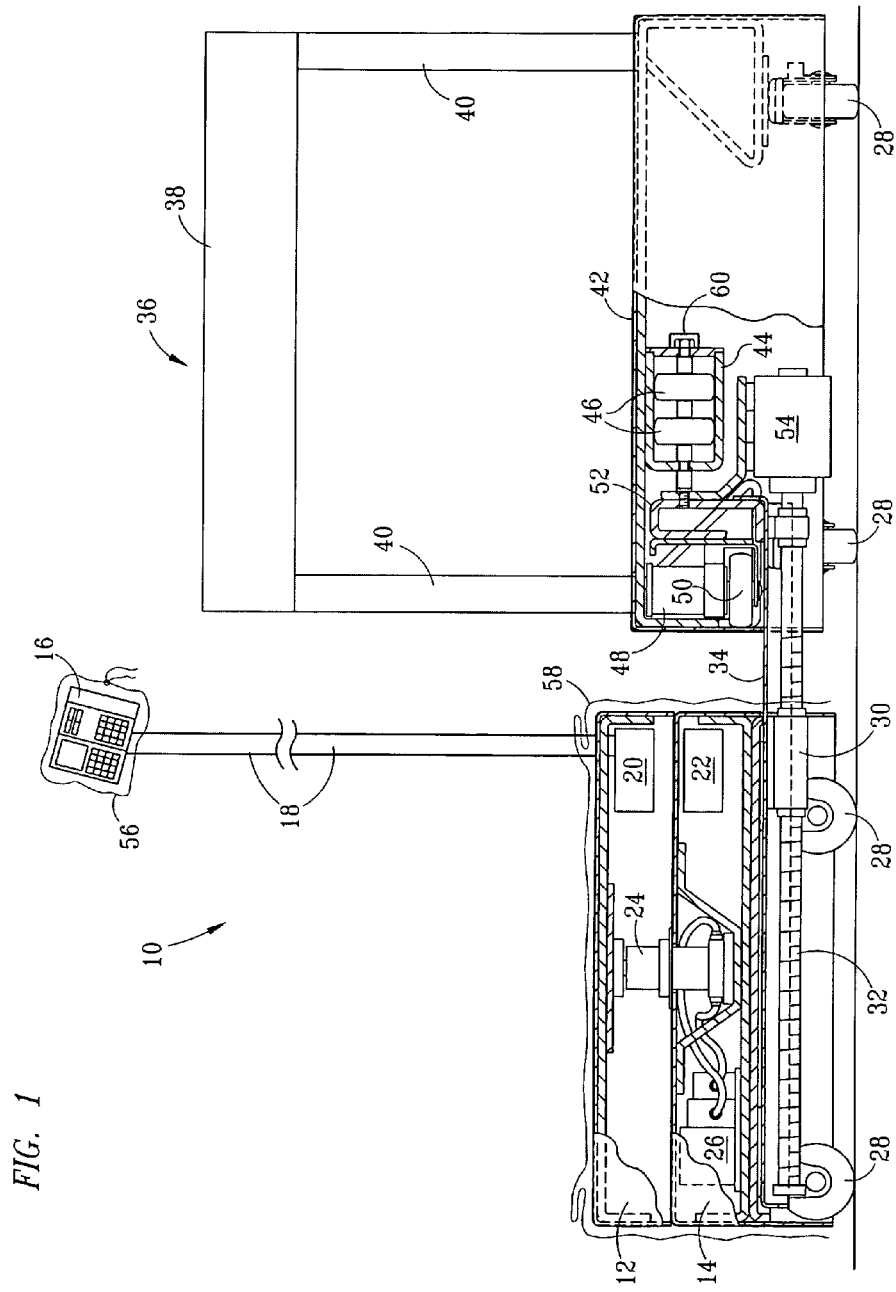
FIG. 1 is a schematic of a preferred first embodiment for a surgeon lift system

FIG. 1 shows a preferred first embodiment of the disclosed surgeon lift for use when a surgeon stands while performing a surgical procedure. The surgeon lift 10 comprises a base 14 equipped with wheels 28 and (foot-actuated) wheel stops (not shown), a platform 12, a hydraulic lift cylinder 24 and hydraulic pump 26, a control pad 16 fixedly attached to the platform 12 via an upright arm support 18, a first electronic circuitry box 20, a second electronic circuitry box 22, and a screw 32 and screw jack securing means 30 operatively connected to a screw motor 54 for regulating the position of the surgeon lift in the x dimension when the surgeon lift is engaged with the surgical table as shown. Shown is the surgeon lift 10 attached to a surgical table via a sliding connector platform 34 that is manually, removably attached to an improved section of the surgical table comprising a surgical table lower support housing 42 installed on the surgical table 36. The purpose of the attachment of the surgeon lift to the surgical table is to enable more precise, and automatic adjustable control of the position of the surgeon lift relative to the surgical table in the x, y, and z directions. Thus, as disclosed in the drawings, a surgical table is improved to contain an assembly that is designed for operative attachment of the connector platform of the surgeon table. Also shown in FIG. 1 are disposable surgical drape 56 for the control pad 16 and a surgical drape 56 for substantially covering the platform 12. Additional surgical drapes may be required in order to properly ready the surgeon lift for the surgical suite.

Figure 2:
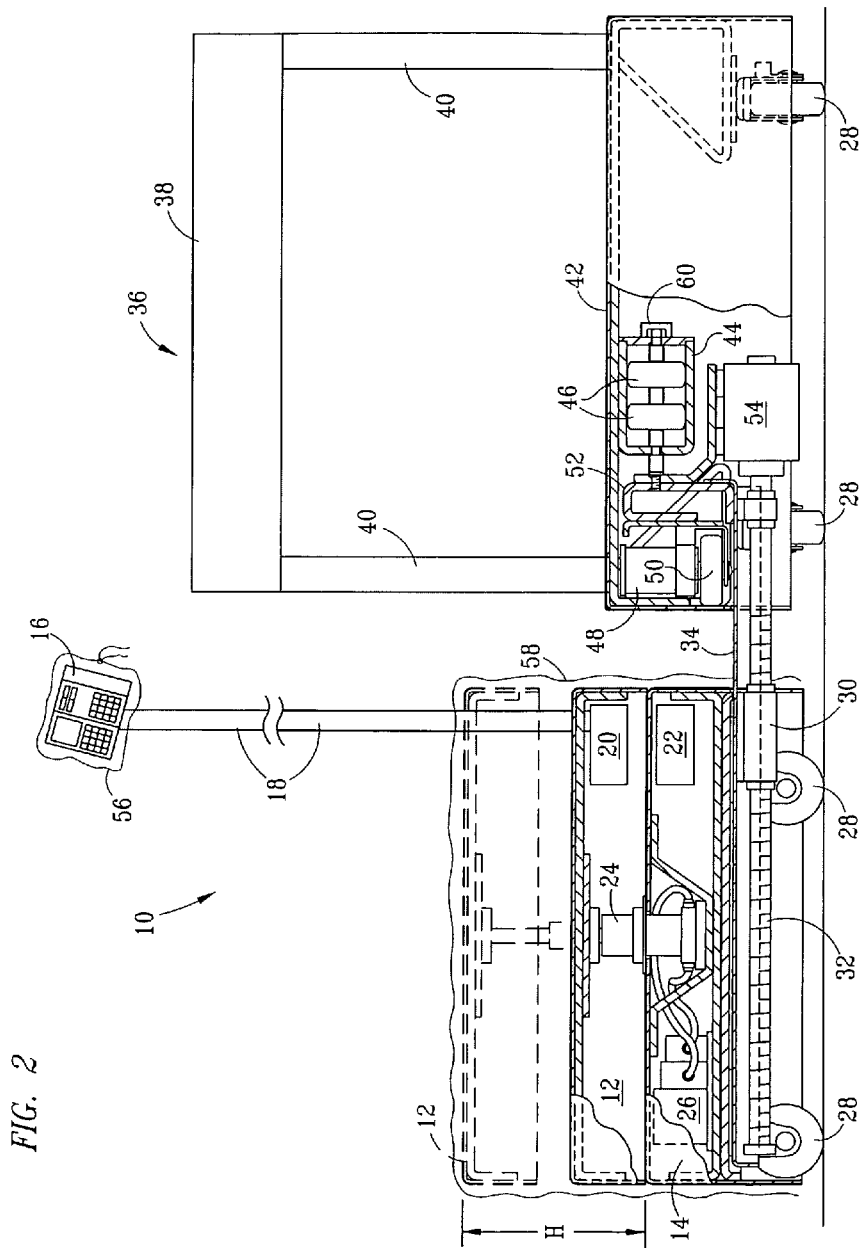
FIG. 2 is a second schematic of a preferred first embodiment for a surgeon lift system

FIG. 2 is a schematic of the preferred first embodiment of the surgeon lift showing the vertical movement of the platform 12 relative to the base 14 of the surgeon lift 10 as the height of the platform is adjusted using the hydraulic lift cylinder/hydraulic pump lifting mechanism. A wide range of vertical movement for the platform is possible to afford needed flexibility in achieving precise surgeon positioning in the y dimension.

Figure 3:
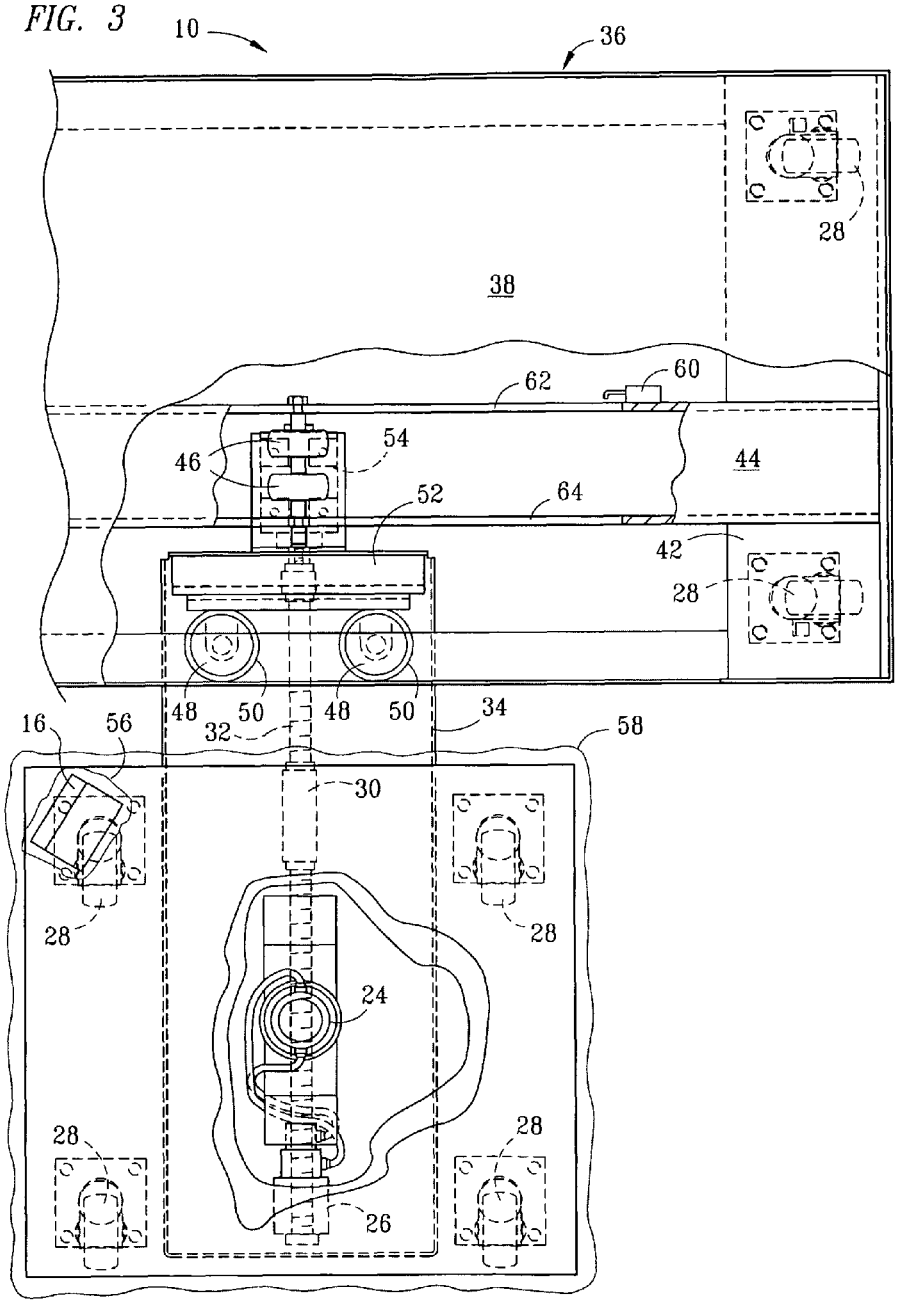
FIG. 3 is a schematic of a top perspective of the preferred embodiment for a surgeon lift system

FIG. 3 is a schematic of a preferred means of attachment of the surgeon lift to a surgical table. The support framework 52 is installed in place using fasteners. The surgeon lift with the screw jack assembly of parts 32, 30 and motor 54 is secured in place with fasteners and is slid into place. The upturned end of sliding connector platform 34 will be secured with fasteners to the support framework 52. A roller support beam 44 comprises a first elongated slot 62 and second elongated slot 64 and limit switch 60 for supporting movement rollers 46 powered by screw motor 54.

Figure 4:
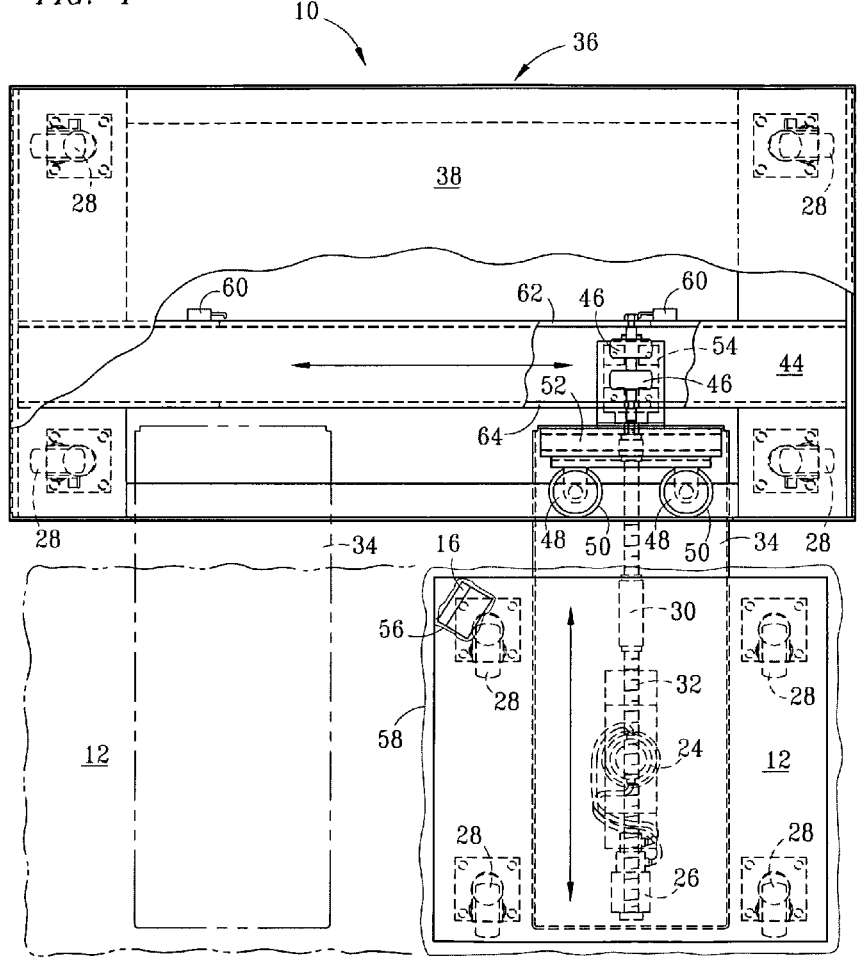
FIG. 4 is a schematic of the surgeon lift—surgical table attachment apparatus per a preferred embodiment

FIG. 4 is a schematic of a surgeon lift—surgical table attachment apparatus per a preferred embodiment. Shown is a surgical table 36 that is improved with a roller support beam 44 which has an attached support framework 52 for powered rollers 50, a synchronous motor 48 for powered rollers 50.

Figure 5A:
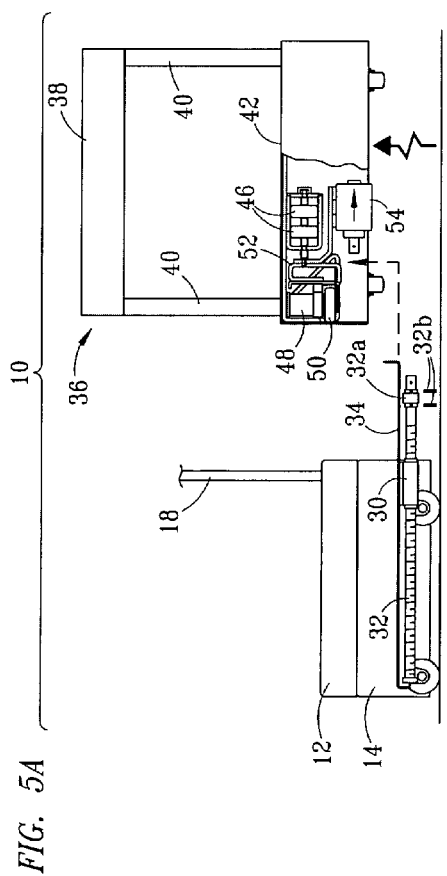
FIG. 5A is a schematic of the surgeon lift system before attachment of the surgeon lift to a surgical table
Figure 5B:
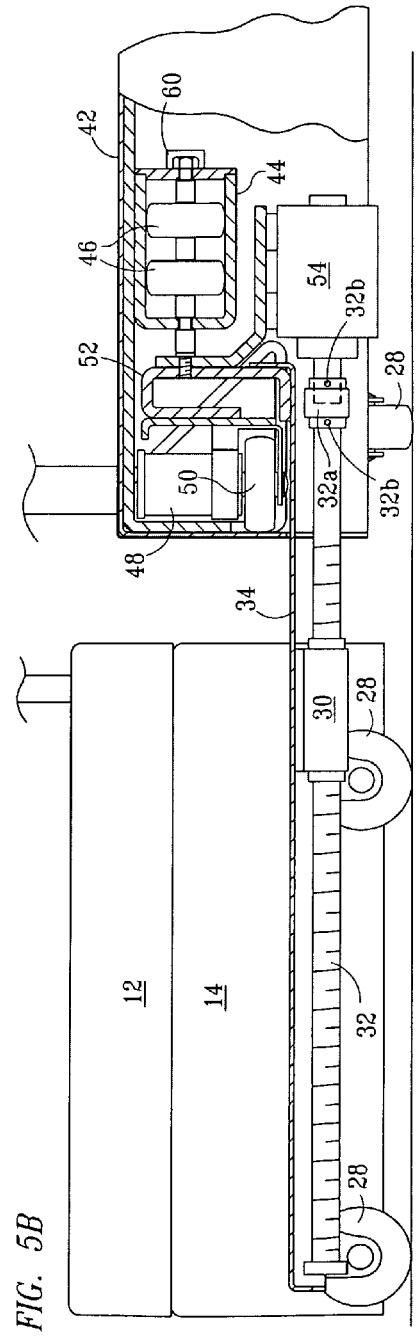
FIG. 5B is a cross-sectional view of the surgeon lift—surgical table attachment apparatus per a preferred embodiment

FIG. 5A is a cross-sectional schematic of a preferred first embodiment of the disclosed surgeon lift system showing the surgeon lift before it is attached to a surgical table 36 that is improved with a lower support housing 42 for operatively engaging the connector platform 34 of the base of the surgeon lift. Shown is a slip coupling 32a and spring pins 32b of the screw jack securing means attached to the screw motor 54.

Figure 6:
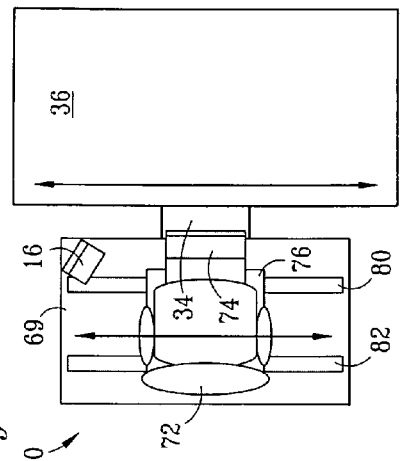
FIG. 6 is a top perspective of a second embodiment of the disclosed surgeon lift
Figure 7:
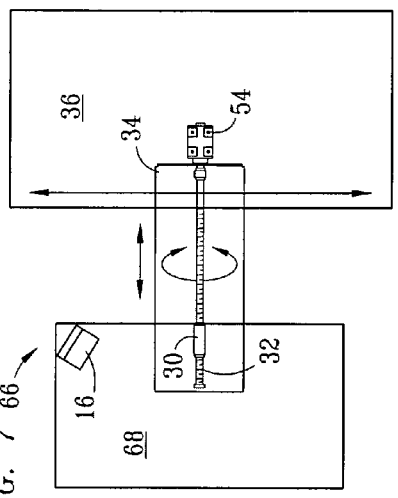
FIG. 7 is a top perspective of the second embodiment of the disclosed surgeon lift system

FIGS. 6 and 7 show a preferred second embodiment of the disclosed surgeon lift with a 'walking' platform 68.

Figure 8:
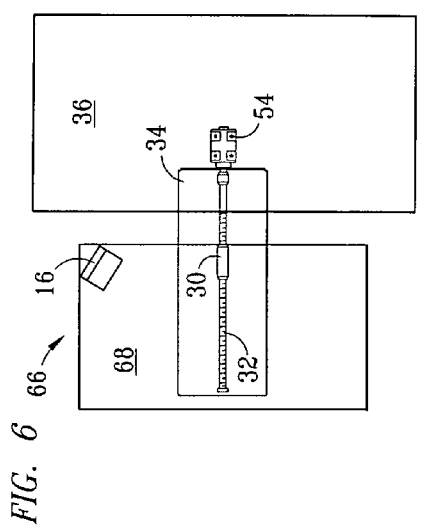
FIG. 8 is a side perspective of a preferred third embodiment of the disclosed surgeon lift with chair combination
Figure 9:
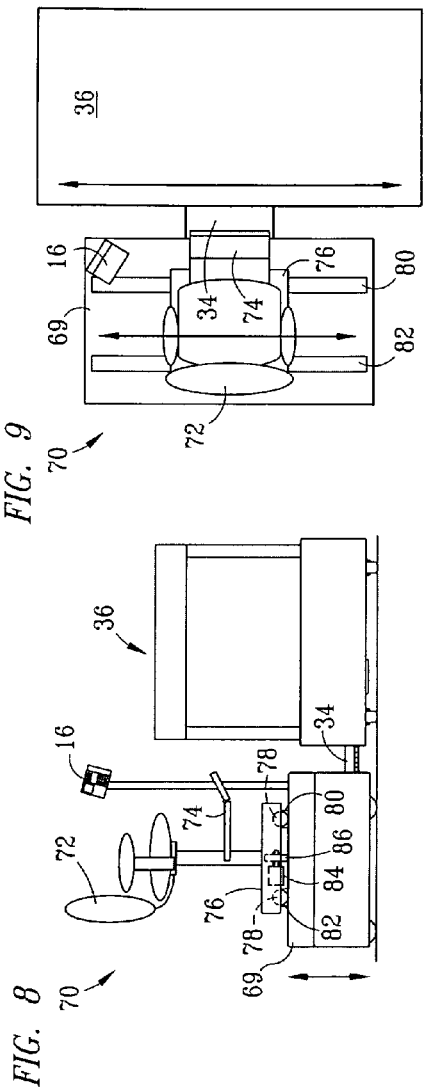
FIG. 9 is top perspective of a preferred third embodiment of the disclosed surgeon lift with chair combination

FIGS. 8 and 9 are side and top perspectives respectively of a preferred third embodiment 70 of the disclosed invention, namely a surgeon lift with chair combination. Shown is a surgeon chair 72 comprising a chair base with wheels 78 attached to a platform 69 comprising wheel guide rails 80 and 82, and equipped with a lift chair drive motor 84 and lift chair drive wheel 86. It is noted that optionally, the chair may be removable and manually attachable to the platform 69 as desired. The surgeon lift platform 69 is specially sized to accommodate a surgeon chair as shown and may be designed to receive more than one surgeon chair. FIGS. 8 and 9 show the surgeon lift attached to the surgical table 36 via a sliding connector platform 34, it is understood that the surgeon lift with chair combination embodiment 70 may also be utilized as a free-moving, standalone system (without attachment to a surgical table) as the surgeon lift is equipped with wheels and wheel brakes.

Although the present invention has been described in terms of certain embodiments, other embodiments apparent to those of ordinary skill in the art also are within the scope of this invention. The system and mechanism for operatively connecting the surgeon lift to a surgical table may vary from the disclosed embodiments while still accomplishing the goal of enabling ready, efficient, and precise, adjustable control of the position of the surgeon lift relative to the surgical table in the x, y, and z dimensions as defined herein. Additionally, the disclosed lift system may be used in non-medical settings as appropriate. Thus, various changes and modifications may be made without departing, from the spirit and scope of the invention.

We claim:

1. A surgeon lift comprising a base, wheels attached to the base, each wheel comprising a locking mechanism, a cylinder supported on the base, a platform operatively connected to the cylinder, a lifting mechanism for adjusting the height of the platform relative to a horizontal surface, a connector attaching of the surgeon lift to a surgical table, and one or more controllers automatically controlling the position of the lift relative to the surgical table in the x, y, and z dimensions, at least one controller comprising pre-defined preferred settings for the position of the surgeon lift relative to the operating table per preferences of at least one surgeon, the settings readily accessed during a set-up of the surgeon lift for an operation to be performed by the at least one surgeon, further comprising at least one surgeon chair attached to the platform, the at least one surgeon chair having at least a pair of wheels and the platform having a pair of wheel guide rails, the surgeon chair manually readily attachable to and detachable from the platform via the at least pair of wheels and wheel guide rails in a sliding motion, the surgeon chair comprising a seat portion and at least one manually operated controller controlling the height of the seat portion relative to the platform, the platform adapted to allow unencumbered movement of a surgeon while in a seated position on the surgeon chair or while walking on the platform as required to perform the operation.

2. The surgeon lift per claim 1 wherein the lifting mechanism allows for height adjustment of the platform in millimeter increments.

3. The surgeon lift per claim 1 wherein at least one of said one or more controller comprises a manually operated pushbutton type control pad.

4. The surgeon lift per claim 1 wherein at least one of said one or more controller is a programmable controller which captures information relative to a surgeon's preferred position for the surgeon lift relative to the surgical table, the information readily accessible during a set-up of the surgeon lift for use in the operating room.

5. The surgeon lift per claim 1 wherein the platform is adapted to allow a surgeon to freely walk on the platform while performing a surgery.

6. The surgeon lift per claim 1 wherein the platform is adapted to accommodate more than one surgeon.

7. The surgeon lift per claim 1 further comprising a controller for adjusting an angle of the platform relative to the horizontal surface.

* * * * *